Figure 1:
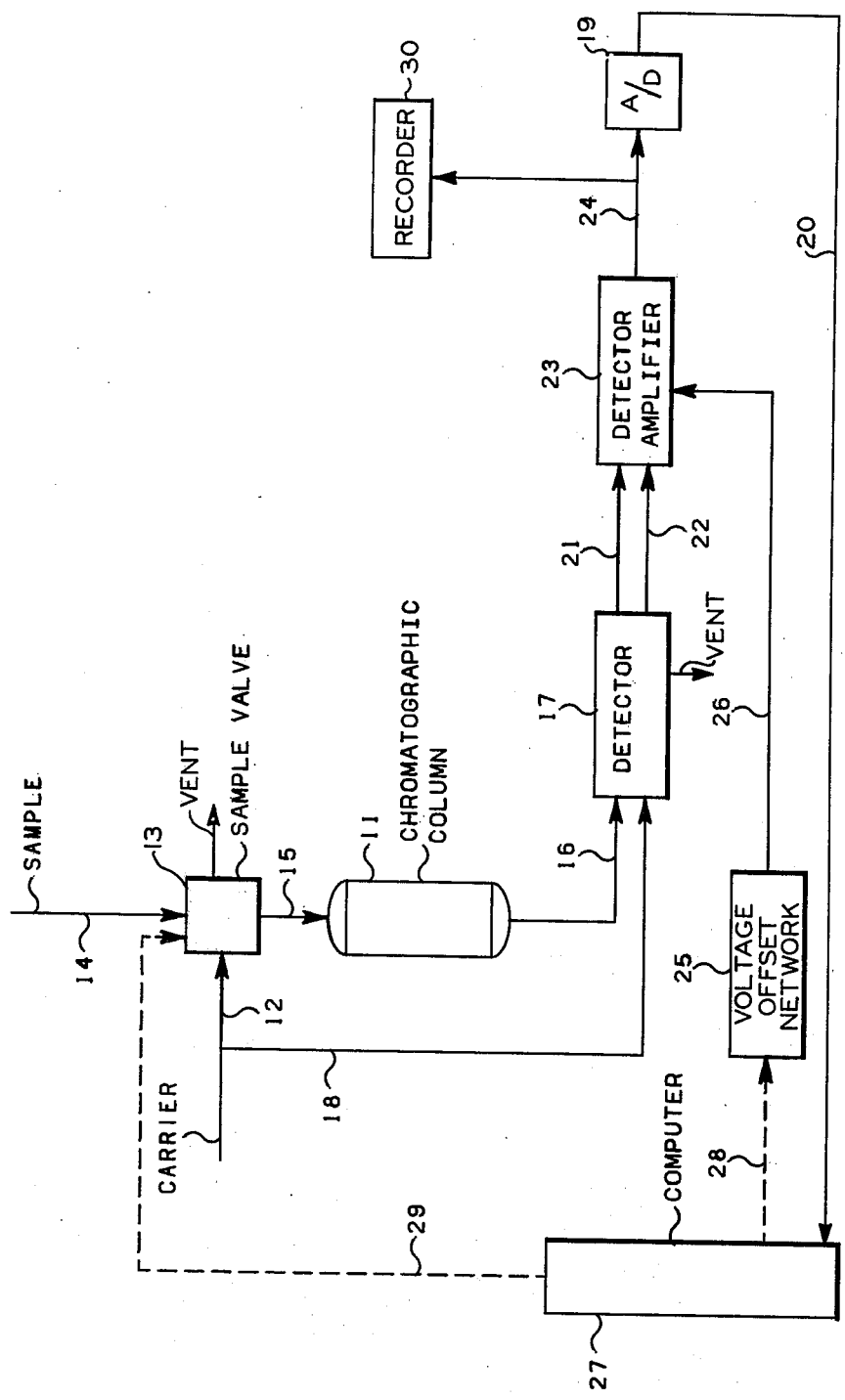

United States Patent [19]

Neer

[11] 4,159,523
[45] Jun. 26, 1979

[54] VOLTAGE OFFSET NETWORK

[75] Inventor: Harold M. Neer, Bartlesville, Okla.

[73] Assignee: Phillips Petroleum Company, Bartlesville, Okla.

[21] Appl. No.: 840,426

[22] Filed: Oct. 7, 1977

[51] Int. Cl.² .................... G06F 11/00; H03K 5/20
[52] U.S. Cl. .................... 364/571; 73/23.1; 307/360; 328/169; 364/497
[58] Field of Search ............ 364/571, 580, 556, 564, 364/552, 554, 497; 340/146.2; 73/23, 23.1; 307/237, 355, 360; 328/147, 169

[56] References Cited

U.S. PATENT DOCUMENTS

| | | | |
|---|---|---|---|
| 3,151,237 | 9/1964 | Hrabak | 364/554 |
| 3,448,291 | 6/1969 | Burk et al. | 307/237 |
| 3,648,071 | 3/1972 | Mrazek | 328/169 |
| 3,659,213 | 4/1972 | Platt | 307/237 |
| 3,683,671 | 8/1972 | Van Swaay | 73/27 R |
| 3,701,908 | 10/1972 | Neer et al. | 307/235 |
| 3,829,786 | 8/1974 | Hoffman et al. | 328/147 |
| 3,845,465 | 10/1974 | Hosick et al. | 340/146.2 |
| 3,882,711 | 5/1975 | Crawford | 73/362 AR |
| 3,882,725 | 5/1975 | Rao et al. | 73/342 |
| 4,063,447 | 12/1977 | Mathison | 364/571 |

Primary Examiner—Felix D. Gruber
Assistant Examiner—Errol A. Krass

[57] ABSTRACT

A voltage offset network is provided for use with systems which produce an analog output signal. The voltage offset network is utilized to automatically reduce or amplify the analog output signal. In this manner the signal level of the analog output signal is made compatible with signal level requirements of other systems with which the system which produced the analog output signal is interfaced.

14 Claims, 2 Drawing Figures

VOLTAGE OFFSET NETWORK

This invention relates to a method and apparatus for automatically reducing or amplifying an analog signal. In one aspect the invention relates to a method and apparatus for controlling the signal level of an analog signal in such a manner that the signal level of the analog signal will be compatible with the requirements of the system to which the analog signal is provided. In a second aspect the invention relates to a method and apparatus for controlling the signal level of an output signal from a detector amplifier associated with a chromatographic analyzer. In a third aspect the invention relates to a method and apparatus for using a digital computer to automatically control the signal level of an output signal from a detector amplifier in such a manner that the output signal level will be compatible with other system requirements.

In many control and measurement systems it is necessary that many different types of equipment be interfaced together. In such systems it is necessary that signal levels be maintained in such a manner that system compatibility is obtained. This is particularly true in the art of chromatography.

In the analysis of fluid mixtures by chromatography, an electrical signal usually is established which is representative of the composition of the effluent stream from a chromatographic column. This signal can be obtained from a bridge network having temperature sensitive resistant elements therein or by a flame ionization detector, for example. The signal is amplified and applied to suitable recording and/or control equipment.

As the applications of chromatography have increased so have the uses of the output electrical signal increased. In some applications the signal level of the output electrical signal is not compatible with either existing plant equipment or with some other system to which the signal is to be applied.

Accordingly, it is an object of this invention to provide a method and apparatus for controlling the signal level of an analog signal in such a manner that the signal level of the analog signal will be compatible with the requirements of the system to which the analog signal is provided.

A second object of this invention to provide a method and apparatus for controlling the signal level of an output electrical signal from a detector amplifier associated with a chromatographic analyzer. Another object of this invention is to provide a method and apparatus for using a digital computer to automatically control the signal level of an output electrical signal from a detector amplifier associated with a chromatographic analyzer in such a manner that the output signal level will be compatible with other system requirements.

In accordance with the prevent invention, as illustrated by the preferred embodiment, a method and apparatus is provided whereby the signal level of the output electrical signal from a detector amplifier associated with a chromatographic analyzer may be increased or decreased as desired. In response to a digital command from a digital computer, a desired voltage level is established by a voltage offset network. This signal is added to or subtracted from one of the input signals to the detector amplifier or from the output signal from the detector amplifier depending on the sign of the signal and in this manner the signal level of the output signal from the detector amplifier may be made compatible with other system requirements.

Figure 2:
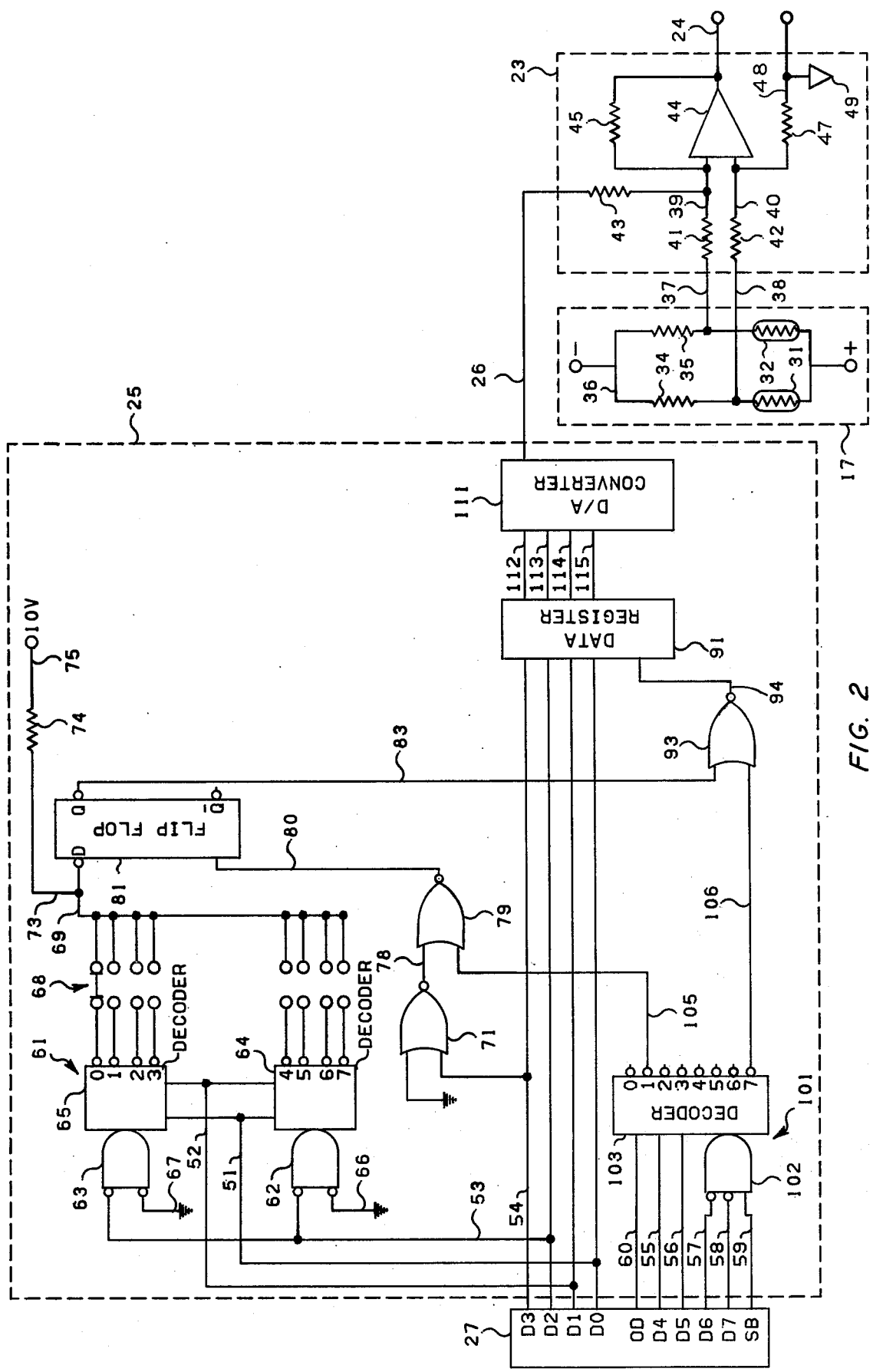

Other objects and advantages of the invention will be apparent from the description of the invention and the appended claims thereto as well as from the detailed description of the drawings in which:

FIG. 1 is representative of a conventional chromatographic analyzer together with a voltage offset network; and FIG. 2 is a schematic of the voltage offset network, the detector, and the detector amplifier illustrated in FIG. 1.

For the sake of simplicity, the invention is illustrated and described in terms of a specific embodiment of a chromatographic analyzer with an associated voltage offset network. Although the invention is illustrated and described in terms of a specific preferred embodiment, the applicability of the invention extends to other embodiments of a chromatographic analyzer wherein it is desired to produce an output signal compatible with some othe system requirements and to other systems which produce analog output signals.

Referring now to the drawings and in particular to FIG. 1, there is shown a chromatographic column 11. A carrier fluid is introduced through conduit means 12 into sample valve 13. A sample of a fluid to be analyzed is delivered to sample valve 13 through conduit means 14. A conduit means 15 extends between sample valve 13 and the inlet to chromatographic column 11. A conduit means 16 extends between the outlet of chromatographic column 11 and the first inlet of a detector means 17. Carrier fluid is passed through the reference portion of detector means 17 by being introduced into the second inlet of detector means 17 through a conduit means 18 which communicates with conduit means 12. Carrier fluid also flows through sample valve 13 and chromatographic column 11 to the first inlet of detector means 17.

At the beginning of an analysis period, sample valve 13 is actuated to introduce a predetermined volume of sample into the carrier fluid flowing through chromatographic column 11. The constituents of the sample are eluted in sequence and flow from chromatographic column 11 through conduit means 16 to the sample portion of detector means 17.

Detector means 17 establishes a differential output by establishing an electrical signal 21 representative of the composition of the carrier fluid carrying the sample passing through the sample portion of detector means 17 and an electrical signal 22 representative of the composition of the carrier gas only in the reference portion of detector means 17. Signals 21 and 22 are then compared by detector amplifier 23 to produce signal 24 which may be supplied to a desired source such as control equipment, recorders, or computers. In the preferred embodiment as illustrated by FIG. 1, signal 24 is supplied to recording means 30.

Because different sources may require different input levels, the voltage offset network 25 reduces or increases the output signal 24 via signal 26 to produce an output signal 24 which has a desired voltage level.

The voltage offset network 25 is controlled by computer means 27 via control signal 28. The sample valve 13 is controlled by computer means 27 via control signal 29.

Control signal 28 is established by computer means 27 in response to signal 20 from A/D converter 19. Signal 24 is supplied to A/D converter 19 which converts signal 24 to a digital signal. Signal 20 from A/D converter 19 will thus be a digital signal representative of the voltage level of signal 24. Computer means 27 utilizes a software program to compare signal 20 to the higher and lower limits established for output signal 24. Based on this comparison signal 28, representative of any required increase or reduction in the voltage level of output signal 24, is established.

FIG. 2 illustrates a preferred embodiment of the detector 17, the detector amplifier 23, and the voltage offset network illustrated in FIG. 1. The control logic utilized to control the balancing network is also shown.

For the sake of convenience, signals which supply power to the various chips shown in the schematic have been omitted. Voltage levels required by various chips are specified by the manufacturers and are well known to those familiar with the art.

Many different circuit configurations are possible which would perform the functions required of the circuit shown in FIG. 2. This is especially true for the logic chips shown because of the many interchangeable chips manufactured by a variety of manufacturers.

The detector means 17 is a thermal conductivity detector in this preferred embodiment. Other types of detectors, such as flame ionization detectors, could also be utilized. Detector means 17 is provided with thermistors 31 and 32. Thermistor 31 is located in the stream of carrier fluid which carries the sample and is termed a sense thermistor. Thermistor 32 is located in the reference stream of the carrier fluid and is termed a reference thermistor. The thermistors 31 and 32 are wired in a bridge circuit with resistors 34 and 35. A constant voltage is applied across the bridge. Current passing through thermistors 31 and 32 heats them. The generated heat is carried away by the fluids flowing past the thermistors. If the eluted components from chromatographic column 11, shown in FIG. 1, have different thermal conductivities than the carrier gas, the temperature of thermistor 31 will vary with the type and quantity of each eluted component. This variation in temperature will result in an unbalance in the bridge circuit and the voltage levels of signals 37 and 38 from the bridge circuit 36 will vary with respect to each other. Signal 37 is supplied through resistor 41 as signal 39 to a first input of amplifier 44. Signal 38 is supplied through resistor 42 as signal 40 to a second input of amplifier 44. The current level of signals 39 and 40 are determined by the voltage levels of signals 26, 37, and 38 and the values of resistors 41, 42, and 43 respectively.

A feedback resistor 45 is connected between the output terminal and the first input terminal of amplifier 44. Signal 40 is also supplied through resistor 47 as a low output signal 48, which in a preferred embodiment is grounded to a high quality ground 49.

The sense element thermistor 31 output is provided to the non-inverting input of amplifier 44. The reference element thermistor 32 output is supplied to the inverting input of amplifier 44. This causes only the difference between signals 39 and 40 to be amplified.

In a preferred embodiment, amplifier 44 has a gain of 10. Resistor elements 41 and 42 have values of 2.35 K$\Omega$. Resistor elements 43, 45 and 47 have values of 23.5 K$\Omega$.

If the voltage level of output signal 24 exceeds the operational limitations of the system to which output signal 24 is being provided, then it is necessary to reduce the voltage level of signal 24 while still maintaining the information carried by signal 24. This is accomplished automatically in the present invention by using the voltage offset network 25.

The digital computer means 27 supplies an eight bit digital address signal plus a clock signal and a data ready signal to the voltage offset network 25. The eight bit digital address signal is labeled D7-D0 in FIG. 2 with D7 representing the most significant bit and D0 representing the least significant bit. The clock signal is represented by the symbol SB. The data ready signal is represented by the symbol OD.

The balancing network 25 must be addressed twice to accomplish its function. In the first address, the flip-flop 81 is set. In the second address, data register 91 is enabled and the data from the digital computer 27 which determines the voltage level of the voltage offset signal 26 is loaded into data register 91.

Signal 51, representative of the least significant bit of the eight bit digital address, is provided as an input to the dual 1-of-4 decoder-demultiplexer 61 which, in a preferred embodiment, is a 74LS156 manufactured by Fairchild Semiconductor. Signal 52, representative of the second least significant bit, and signal 53, representative of the third least significant bit, are also supplied as inputs to the dual 1 of 4 decoder-demultiplexer 61. Signals 51, 52, and 53 are also supplied as inputs to data register 91. Signal 54, representative of the fourth least significant bit, is supplied as an input to data register 91 and is also supplied as a first input to NOR gate means 71. Signals 55-58, representative of the four most significant bits with signal 58 representing the most significant bit of the eight bit digital address, are supplied to the 1-of-8 decoder/demultiplexer 101. Signal 59 representative of the clock signal and signal 60 representative of the data ready signal are also supplied as inputs to the 1 of 8 decoder/demultiplexer 101. In a preferred embodiment the 1-of-8 decoder/demultiplexer 101 is a 74LS138 manufactured by Fairchild Semiconductor.

In a first digital address, flip-flop 81 is set. In this preferred embodiment because of the strapping and the circuit configuration, a first digital address signal having a binary pattern of 00001000 is necessary to set output signal 83 from flip-flop 81 equal to logic 0 (low).

Signals 51-53 having a binary pattern of 000 are supplied to the dual 1 of 4 decoder/demultiplexer 61. As is shown in FIG. 2, dual 1 of 4 decoder 61 is made up of AND gates 62 and 63 and decoders 64 and 65. Signals 51 and 52 are supplied to decoders 64 and 65. Signal 53 is supplied as one input to AND gates 62 and 63. The second input signals 66 and 67 to AND gates 62 and 63 are held low by grounding these inputs. The second inputs to AND gates 62 and 63 are inverted as shown. The first input to AND gate 63 is also inverted. All of the outputs of decoders 64 and 65 are also inverted as shown.

When the output of AND gate 62 is equal to logic 1 (high), the decoder 64 is enabled. When the output of AND gate 63 is high, the decoder 65 is enabled. The output of AND gate 63 will go high when signal 53 is low; thus for a first digital address signal where the three least significant bits have a binary pattern of 000, decoder 65 will be enabled and the output terminal labeled 0 of decoder 65 will be selected because this is the binary number represented by the two least significant bits of the first digital address signal. As is shown, strapping means 68 is strapped so that the 0 output terminal of decoder 65 is connected to signal line 69.

It should be noted that if it is desired to control a number of voltage offset networks 25, where each voltage offset network is utilized by a different detector amplifier, it is simply necessary to change the strapping of strapping means 71. In this manner, the same digital computer means can be utilized to control a plurality of voltage offset networks utilizing the same digital address lines and simply changing the binary pattern of the digital address signal to enable a desired voltage offset network. For the sake of simplicity and ease of illustration, the present invention is described in terms of only one voltage offset network and one detector amplifier but the invention is not limited in its scope to this configuration.

Signal 69 is supplied as a first input to flip-flop 81. Signal 69 is held high by signal 73. The current level of signal 73 is determined by signal 75, which in a preferred embodiment has a voltage level of 10 V, and resistor 74. When the 0 output terminal is selected by decoder 65, it will go high but will be inverted as shown so that in effect it is low. Decoder 65 will then act as a current sink and signal 73 will flow into decoder 65 which is acting as a ground. This will force signal 69 to go low. Signal 54, which is high when it is desired to set signal 83 from flip-flop 81 low, is supplied as a first input to NOR gate 71. The second input signal, 77, to NOR gate 71 is held low by grounding this input. When signal 54 is high, signal 78 from NOR gate 71 will be low and is supplied as one input to AND gate 79.

Signals 55-58, which represent the four most significant bits of the first digital address signal, have a binary pattern of 0000 in this preferred embodiment when it is desired to set the output signal 83 from flip-flop 81 low, and are supplied to the 1-of-8 decoder/demultiplexer 101. A clock signal 59, which is high, and a data ready signal 60, which is high when data is available to be supplied to data register 91, are also supplied to the 1 of 8 decoder/demultiplexer 101.

As is shown in FIG. 2, the 1 of 8 decoder/demultiplexer 101 is made up of AND gate 102 and decoder 103. The two most significant bits of the first digital address signal, signals 57 and 58, are supplied as first and second inputs to AND gate 102. The clock signal 59 is supplied as a third input to AND gate 102. The first and second inputs of AND gate 102 are inverted as shown. The output of AND gate 102 will go high when the clock signal 59 goes high thus enabling decoder 103.

Signals 55, 56, and 60 are supplied to decoder 103. Signal 60 occupies the spot of the least significant bit; thus, when signal 60 is high and signals 55 and 56 are low, the output terminal labeled 1 will go high but, because all the output terminals of decoder 103 are inverted as shown, signal 105 from decoder 103 will be low. Signal 105 is supplied as a second input to NOR gate 79.

When signals 78 and 105 are both low, the output signal 80 from NOR gate 79 will be high. Signal 80 is supplied as a second input to flip-flop 81.

The first input to flip-flop 81 is inverted as shown and is labeled D. In a preferred embodiment flip-flop 81 is a 74LS74 by Fairchild Semiconductor. When signal 80 goes high the state of the D input of flip-flop 81 is transferred to the Q output of flip-flop 81. Thus the output labeled Q of flip-flop 81 will go high but signal 83 will be low because both output terminals of flip-flop 81 are inverted. Signal 83 is supplied as a first input to NOR gate 93.

A second digital address signal is now supplied to the voltage offset network 25. The three least significant bits are to determine the voltage level of output signal 26 from the voltage offset network 25. The fourth least significant bit determines the sign of signal 26. The four most significant bits enable data register 91. For the sake of illustration, a second digital address, having a binary pattern of 00111011, will be utilized. Signals 59 and 60 remain high.

Decoder 103 will be enabled when the clock signal 59 is high which will allow the binary pattern of signals 55, 56, and 60 to be decoded. Since, in this example, signals 55, 56, and 60 have a binary pattern of 111, the output terminal labeled 7 of decoder 103 will go high but signal 106 from decoder 103 will be low because of the inversion shown. Signal 106 is supplied as a second input to NOR gate 93. Note that signal 83 which is supplied as a first input to NOR gate 93 is still low because signal 105 from decoder is now high and flip-flop 81 will not change states.

Output signal 94 from AND gate 93 will be high when signals 83 and 106 are low. Signal 94 is supplied as an enabling signal to data register 91. When signal 94 is high, data register 91 is enabled and signals 51-54 are loaded. Signals 51-54 are transferred to D/A converter 111 via output signals 112-115 from data register 91.

The voltage level and sign of signal 26 is determined by the binary pattern of signals 112-115. In this preferred embodiment, signal 112 corresponds to signal 54 and is utilized to set the sign of signal 26. Signals 113-115 correspond to signals 51-53 respectively and are utilized to determine the voltage level of signal 26.

Signal 26 has a voltage range of 0 to ±8.4 V in this preferred embodiment. When signal 112 is high, the sign of signal 26 is positive; when signal 112 is low, the sign of signal 26 is negative. The absolute value of the voltage level is determined as shown in the table below.

| D2 4.8V | D1 2.4V | D0 1.2V | Voltage Level of Signal 26 |
|---|---|---|---|
| 0 | 0 | 0 | 0 |
| 0 | 0 | 1 | 1.2 |
| 0 | 1 | 0 | 2.4 |
| 0 | 1 | 1 | 3.6 |
| 1 | 0 | 0 | 4.8 |
| 1 | 0 | 1 | 6.0 |
| 1 | 1 | 0 | 7.2 |
| 1 | 1 | 1 | 8.4 |

In this example, for a second digital address of 00111011, the voltage level of signal 26 would be +3.6 V. This voltage level is provided across resistor 43 and in this case would increase the level of signal 39.

Many of the specific components which may be utilized in the practice of the invention as illustrated by FIGS. 1 and 2 have been specified in the description. Other specific components are as follows:

| | |
|---|---|
| A/D converter 19 | AD 7550, Analog Devices Inc. Norwood, Mass. |
| Thermistors 31 and 32 | AX1775 (8K-Pair, Matched) Veco, Inc., Springfield, N.J. 07081 |
| NOR gate 71 | 74 LS 02 Fairchild Semiconductor Mountain View, California |
| NOR gates 79 and 93 | 74 LS 02 Fairchild Semiconductor Mountain View, California |
| Data register 91 | 74 LS 175 Fairchild Semiconductor Mountain View, California |
| D/A converter 111 | AD 561K, Analog Devices Inc. Norwood, Mass. 02062 |
| Amplifier 44 | OP-05, Precision Monolithics, Inc. Santa Clara, Ca. 95050 |
| Computer 27 | M6800 |

Resistance values were previously specified and are readily available from a number of manufacturers.

While the invention has been described in terms of the presently preferred embodiments, reasonable variations and modifications are possible by those skilled in the art, within the scope of the described invention and the appended claims.

That which is claimed is:

1. A voltage offset network adapted for use in a system which outputs an analog signal comprising:
   means for establishing a first signal representative of the voltage level of said analog signal;
   means for establishing a second signal representative of the highest allowable voltage level for said analog signal;
   means for establishing a third signal representative of the lowest allowable voltage level for said analog signal;
   means for comparing said first signal to said second signal and said third signal and for establishing a fourth signal responsive to the comparison;
   means for establishing, responsive to said fourth signal, an offset signal having a desired voltage level; and
   means for combining said offset signal and said analog signal in such a manner that the voltage level of said analog signal, represented by said first signal, will not go above the limit represented by said second signal and will not go below the limit represented by said third signal.

2. Apparatus in accordance with claim 1 wherein said means for establishing said first signal is an analog-to-digital converter means.

3. Apparatus in accordance with claim 1 wherein said means for comparing said first signal to said second signal and said third signal and for establishing said fourth signal responsive to the comparison is a digital computer means.

4. Apparatus in accordance with claim 1 wherein said means for establishing said offset signal is a digital-to-analog converter means.

5. Apparatus in accordance with claim 1 wherein said means for establishing said offset signal comprises
   a digital computer means for establishing said fourth signal which is a digital command signal utilized to determine the voltage level of said offset signal, said fourth signal consisting of a plurality of bits; for establishing a fifth signal which is a digital command signal utilized as an enabling signal, said fifth signal consisting of a plurality of bits; for establishing a sixth signal which is a clock signal; and for establishing a seventh signal which is a data ready signal;
   data register means;
   means for providing a first plurality of the bits of said fourth signal to said data register means;
   means for enabling said data register means to load said first plurality of the bits of said fourth signal in response to the combination of said fifth, sixth and seventh signals and a second plurality of the bits of said fourth signal;
   digital-to-analog converter means; and
   means for providing said first plurality of the bits of said fourth signal to said digital-to-analog converter means to therein establish said offset signal in response to said first plurality of the bits of said fourth signal.

6. Apparatus in accordance with claim 5 wherein said means for enabling said data register means to load said first plurality of the bits of said fourth signal in response to the combination of said fifth, sixth and seventh signals and said second plurality of the bits of said fourth signal comprises:
   dual 1-of-4 decoder-demultiplexer means having a plurality of input terminals and a plurality of output terminals;
   flip-flop means having a plurality of input terminals and a plurality of output terminals;
   means for establishing an eighth signal which has a first logic state and means for supplying said eighth signal to a first one of said plurality of input terminals of said flip-flop means;
   means for supplying a first plurality of the bits of said fifth signal to said dual 1-of-4 decoder-demultiplexer means to therein drive a first one of said plurality of output terminals of said dual 1-of-4 decoder-demultiplexer means to a second logic state in response to said first plurality of the bits of said fifth signal;
   strapping means for strapping the one of the output terminals of said dual 1-of-4 decoder-demultiplexer means which was driven to said second logic state to the first input terminal of said flip-flop means;
   means for inverting the signal supplied to said first one of said plurality of input terminals of said flip-flop means to drive said first one of said plurality of input terminals of said flip-flop means to said first logic state;
   first NOR gate means having a plurality of input terminals and on output terminal;
   means for supplying a predetermined bit of said fifth signal, which has a logic value corresponding to said first logic state when it is desired to enable said data register means, to a first one of said plurality of input terminals of said first NOR gate means;
   means for grounding a second one of said plurality of input terminals of said first NOR gate means to hold the second one of said plurality of input terminals of said first NOR gate means at said second logic state;
   second NOR gate means having a plurality of input terminals and an output terminal;
   means for supplying the output signal from said first NOR gate means, which has a logic value corresponding to said second logic state, to a first one of said plurality of the input terminals of said second NOR gate means;
   1-of-8 decoder/demultiplexer means having a plurality of input terminals and a plurality of output terminals;
   means for supplying a second plurality of bits of said fifth signal and said sixth and seventh signals to said 1-of-8 decoder/demultiplexer means to therein drive a first one of said plurality of output terminals of said 1-of-8 decoder/demultiplexer means to said first logic state in response to said second plurality of bits of said fifth signal and said sixth and seventh signals;
   means for inverting the output signal from said first one of said plurality of output terminals of said 1-of-8 decoder/demultiplexer means and for supplying a ninth signal, which has a logic value corresponding to said second logic state, from said first one of said plurality of output terminals of said 1-of-8 decoder/demultiplexer means to a second one of said plurality of input terminals of said second NOR gate means;

means for supplying the output signal from said second NOR gate means, which has a logic value corresponding to said first logic state, to a second one of said plurality of input terminals of said flip-flop means to therein change the state of a first one of said plurality of output terminals of said flip-flop means to said first logic state;

third NOR gate means having a plurality of input terminals and an output terminal;

means for inverting the output signal from said first one of said plurality of output terminals of said flip-flop means and for providing a tenth signal, which has a logic value corresponding to said second logic state, to a first one of said plurality of input terminals of said third NOR gate means;

means for supplying said second plurality of bits of said fourth signal to said 1-of-8 decoder/demultiplexer means to therein drive a second one of said plurality of output terminals of said 1-of-8 decoder/demultiplexer means to said first logic state in response to the second plurality of bits of said fourth signal and to return said first one of said plurality of output terminals of said 1-of-8 decoder/demultiplexer means to said second logic state;

means for inverting said second one of said plurality of the output terminals of said 1-of-8 decoder/demultiplexer means and for supplying an eleventh signal, which has a logic value corresponding to said second logic state, from said second one of said plurality of the output terminals of said 1-of-8 decoder/demultiplexer means to a second one of said plurality of input terminals of said third NOR gate means; and means for supplying the output signal, which has a logic value which corresponds to said first logic state, from said third NOR gate means to said data register means to enable said data register means to load said first plurality of bits of said fourth signal.

7. Apparatus in accordance with claim 1 wherein said system which outputs said analog signal comprises:
an amplifier means;
a chromatographic analyzer means for establishing a fifth signal representative of the composition being analyzed by said chromatographic analyzer means and for establishing a sixth signal to be used as a reference signal; and
means for supplying said fifth signal and said sixth signal as inputs to said amplifier means to therein amplify the difference between said fifth signal and said sixth signal to provide said analog signal representative of the amplified difference between said fifth signal and said sixth signal.

8. A method for altering the magnitude of an analog signal output by a system comprising the steps of:
establishing a first signal representative of the voltage level of said analog signal;
establishing a second signal representative of the highest allowable voltage level for said analog signal;
establishing a third signal representative of the lowest allowable voltage level for said analog signal;

comparing said first signal to said second signal and said third signal and establishing a fourth signal responsive to the comparison;
establishing, responsive to said fourth signal, an offset signal having a desired voltage level; and
combining said offset signal and said analog signal in such a manner that the voltage level of said analog signal, represented by said first signal, will not go above the limit represented by said second signal and will not go below the limit represented by said third signal.

9. A method in accordance with claim 8 wherein said step of establishing said first signal comprises converting said analog signal from analog form to said first signal which is digital in form in such manner that the binary pattern of said first signal is representative of the voltage level of said analog signal.

10. A method in accordance with claim 8 wherein said step of comparing said first signal and said second signal and said third signal and establishing a fourth signal responsive to the comparison comprises:
utilizing a software program for a digital computer means to make the comparison; and
establishing said fourth signal as a digital command signal from said digital computer means in response to the comparison.

11. A method in accordance with claim 8 wherein said step of establishing said offset signal comprises converting said fourth signal from digital form to said offset signal which is in analog form in such a manner that said offset signal is representative of the amount by which it is desired to alter said analog signal.

12. A method in accordance with claim 8 wherein said step of establishing said offset signal comprises:
establishing said fourth signal as a digital command signal from a digital computer means utilized to determine the voltage level of said offset signal, said fourth signal consisting of a plurality of bits;
establishing a fifth signal which is a clock signal;
establishing a sixth signal which is a data ready signal;
establishing a seventh signal which is a digital command signal utilized as an enabling signal, said seventh signal consisting of a plurality of bits;
providing a first plurality of bits of said fourth signal to a data register means;
enabling said data register means to load said first plurality of bits of said fourth signal in response to the combination of said fifth, sixth and seventh signals and a second plurality of bits of said fourth signal; and
providing said first plurality of bits of said fourth signal to a digital to analog converter means to therein establish said offset signal in response to said first plurality of bits of said fourth signal.

13. A method in accordance with claim 12 wherein said step of enabling said data register means to load said first plurality of bits of said fourth signal in response to the combination of said fifth, sixth and seventh signals and said second plurality of bits of said fourth signal comprises:
supplying a first plurality of bits of said seventh signal to a dual 1-of-4 decoder/demultiplexer means to therein drive a first one of a plurality of output terminals of said dual 1-of-4 decoder/demultiplexer means to a second logic state in response to said first plurality of bits of said seventh signal;

establishing an eighth signal which has a first logic state and supplying said eighth signal to a first one of a plurality of input terminals of a flip-flop means;

strapping said first one of said plurality of output terminals of said dual 1-of-4 decoder/demultiplexer means, which was driven to said second logic state, to said first one of said plurality of input terminals of said flip-flop means;

inverting the signal supplied to said first one of said plurality of input terminals of said flip-flop means to drive said first one of said plurality of input terminals of said flip-flop means to said first logic state;

supplying a predetermined bit of said seventh signal, which has a logic value corresponding to said first logic state when it is desired to enable said data register means, to a first one of a plurality of input terminals of a first NOR gate means;

grounding a second one of said plurality of input terminals of said first NOR gate means to hold said second one of said plurality of input terminals of said NOR gate means at said second logic state;

supplying the output signal from said NOR gate means, which has a logic value corresponding to said second logic state, to a first one of a plurality of input terminals of a second NOR gate means;

supplying a second plurality of bits of said seventh signal and said fifth and sixth signals of a 1-of-8 decoder/demultiplexer means to therein drive a first one of a plurality of output terminals of said 1-to-8 decoder/demultiplexer means to said first logic sate in response to said second plurality of bits of said seventh signal and said fifth, and sixth signals;

inverting the output signal from said first one of said plurality of output terminals of said 1-of-8 decoder/demultiplexer means and supplying a ninth signal, which has a logic state corresponding to said second logic state, from said first one of said plurality of output terminals of said 1-of-8 decoder/demultiplexer means to a second one of said plurality of input terminals of said second NOR gate means;

supplying the output signal from said second NOR gate means, which has a logic state corresponding to said first logic state, to a second one of said plurality of input terminals of said flip-flop means to therein change the state of a first one of the plurality of output terminals of said flip-flop means to said first logic state;

inverting the output signal from said first one of said plurality of output terminals of said flip-flop means and providing a tenth signal, which has a logic state corresponding to said second logic state, to a first one of a plurality of input terminals of a third NOR gate means;

supplying said second plurality of bits of said fourth signal to said 1-of-8 decoder/demultiplexer means to therein drive a second one of said plurality of output terminals of said 1-of-8 decoder/demultiplexer means to said first logic state in response to said second plurality of bits of said fourth signal and to return said first one of said plurality of output terminals of said 1-of-8 decoder/demultiplexer means to said second logic state;

inverting the output signal from said second one of said plurality of output terminals of said 1-of-8 decoder/demultiplexer means and supplying an eleventh signal, which has a logic state corresponding to said second logic state, from said second one of said plurality of output terminals of said 1-of-8 decoder/demultiplexer means to a second one of said plurality of input terminals of said third NOR gate means; and supplying the output signal, which has a logic state corresponding to said first logic state, from said third NOR gate means to said data register means to enable said data register means to load said first plurality of bits of said fourth signal.

14. A method in accordance with claim 8 wherein said analog signal is established by:

establishing a fifth signal representative of the composition being analyzed by a chromatographic analyzer;

establishing a sixth signal to be used as a reference signal; and supplying said fifth signal and said sixth signal as inputs to an amplifier means to therein amplify the difference between said fifth signal and said sixth signal to establish said analog signal representative of the amplified difference between said fifth signal and said sixth signal.

* * * * *